(12) United States Patent
Heruth et al.

(10) Patent No.: US 7,775,993 B2
(45) Date of Patent: Aug. 17, 2010

(54) DETECTING SLEEP

(75) Inventors: Kenneth T. Heruth, Edina, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 11/081,786

(22) Filed: Mar. 16, 2005

(65) Prior Publication Data

US 2005/0222522 A1    Oct. 6, 2005

Related U.S. Application Data

(63) Continuation-in-part of application No. 10/825,964, filed on Apr. 15, 2004.

(60) Provisional application No. 60/553,771, filed on Mar. 16, 2004.

(51) Int. Cl.
- A61B 5/103 (2006.01)
- A61B 5/117 (2006.01)
- A61B 5/08 (2006.01)
- A61B 5/05 (2006.01)

(52) U.S. Cl. .................. 600/587; 600/532; 600/533; 600/534; 600/547

(58) Field of Classification Search .............. 600/301, 600/587, 549, 529, 534, 533, 547, 532; 900/547; 340/575
See application file for complete search history.

(56) References Cited

U.S. PATENT DOCUMENTS

| | | | |
|---|---|---|---|
| 4,297,685 A * | 10/1981 | Brainard, II | 340/575 |
| 4,550,736 A | 11/1985 | Broughton et al. | |
| 4,771,780 A | 9/1988 | Sholder | |
| 4,776,345 A | 10/1988 | Cohen et al. | |
| 4,846,195 A | 7/1989 | Alt | |
| 5,040,536 A | 8/1991 | Riff | |
| 5,058,584 A | 10/1991 | Bourgeois | |

(Continued)

FOREIGN PATENT DOCUMENTS

DE    198 31 109    1/2000

(Continued)

OTHER PUBLICATIONS

M.T. Smith et al., "Presleep Cognitions in Patients with Insomnia Secondary to Chronic Pain," Journal of Behavioral Medicine, vol. 24, No. 1, pp. 93-114, 2001.

(Continued)

*Primary Examiner*—Max Hindenburg
*Assistant Examiner*—Jeffrey G Hoekstra
(74) *Attorney, Agent, or Firm*—Shumaker & Sieffert, P.A.

(57) ABSTRACT

A system includes one or more sensors and a processor. Each of the sensors generates a signal as a function of at least one physiological parameter of a patient that may discernibly change when the patient is asleep. The processor monitors the physiological parameters, and determines whether the patient is asleep based on the parameters. In some embodiments, the processor determines plurality of sleep metric values, each of which indicates a probability of the patient being asleep, based on each of a plurality of physiological parameters. The processor may average or otherwise combine the plurality of sleep metric values to provide an overall sleep metric value that is compared to a threshold value in order to determine whether the patient is asleep.

7 Claims, 4 Drawing Sheets

U.S. PATENT DOCUMENTS

| | | | |
|---|---|---|---|
| 5,125,412 | A | 6/1992 | Thornton |
| 5,154,180 | A | 10/1992 | Blanchet et al. |
| 5,233,984 | A | 8/1993 | Thompson |
| 5,275,159 | A | 1/1994 | Griebel |
| 5,335,657 | A | 8/1994 | Terry, Jr. et al. |
| 5,337,758 | A | 8/1994 | Moore et al. |
| 5,342,409 | A | 8/1994 | Mullett |
| 5,469,861 | A | 11/1995 | Piscopo et al. |
| 5,476,483 | A | 12/1995 | Bornzin et al. |
| 5,514,162 | A | 5/1996 | Bornzin et al. |
| 5,593,431 | A | 1/1997 | Sheldon |
| 5,622,428 | A | 4/1997 | Bonnet |
| 5,645,053 | A * | 7/1997 | Remmers et al. ....... 128/204.23 |
| 5,732,696 | A * | 3/1998 | Rapoport et al. ............ 600/301 |
| 5,782,884 | A | 7/1998 | Stotts et al. |
| 5,895,371 | A | 4/1999 | Levitas et al. |
| 5,904,708 | A | 5/1999 | Goedeke |
| 5,919,149 | A | 7/1999 | Allum |
| 5,941,906 | A | 8/1999 | Barreras, Sr. et al. |
| 5,944,680 | A | 8/1999 | Christopherson et al. |
| 5,999,846 | A | 12/1999 | Pardey et al. |
| 6,044,297 | A | 3/2000 | Sheldon et al. |
| 6,045,513 | A | 4/2000 | Stone et al. |
| 6,059,576 | A | 5/2000 | Brann |
| 6,095,991 | A | 8/2000 | Krausman et al. |
| 6,102,874 | A | 8/2000 | Stone et al. |
| 6,120,467 | A | 9/2000 | Schallhorn |
| 6,128,534 | A | 10/2000 | Park et al. |
| 6,157,857 | A | 12/2000 | Dimpfel |
| 6,165,143 | A | 12/2000 | van Lummel |
| 6,259,948 | B1 | 7/2001 | Florio et al. |
| 6,280,409 | B1 | 8/2001 | Stone et al. |
| 6,296,606 | B1 | 10/2001 | Goldberg et al. |
| 6,308,098 | B1 | 10/2001 | Meyer |
| 6,351,672 | B1 | 2/2002 | Park et al. |
| 6,366,813 | B1 | 4/2002 | DiLorenzo |
| 6,416,471 | B1 | 7/2002 | Kumar et al. |
| 6,440,090 | B1 | 8/2002 | Schallhorn |
| 6,449,508 | B1 | 9/2002 | Sheldon et al. |
| 6,459,934 | B1 | 10/2002 | Kadhiresan |
| 6,466,821 | B1 | 10/2002 | Pianca et al. |
| 6,468,234 | B1 | 10/2002 | Van der Loos et al. |
| 6,514,218 | B2 * | 2/2003 | Yamamoto .................. 600/587 |
| 6,539,249 | B1 | 3/2003 | Kadhiresan et al. |
| 6,574,507 | B1 | 6/2003 | Bonnet |
| 6,605,038 | B1 | 8/2003 | Teller et al. |
| 6,611,783 | B2 | 8/2003 | Kelly, Jr. et al. |
| 6,659,968 | B1 | 12/2003 | McClure |
| 6,687,538 | B1 | 2/2004 | Hrdlicka et al. |
| 6,731,984 | B2 | 5/2004 | Cho et al. |
| 6,752,766 | B2 | 6/2004 | Kowallik et al. |
| 6,773,404 | B2 * | 8/2004 | Poezevera et al. ............ 600/534 |
| 6,819,956 | B2 | 11/2004 | DiLorenzo |
| 6,878,121 | B2 * | 4/2005 | Krausman et al. ........... 600/587 |
| 6,881,192 | B1 | 4/2005 | Park |
| 6,884,596 | B2 | 4/2005 | Civelli et al. |
| 6,890,306 | B2 | 5/2005 | Poezevera |
| 6,928,324 | B2 | 8/2005 | Park et al. |
| 6,964,641 | B2 | 11/2005 | Cho et al. |
| 7,162,304 | B1 | 1/2007 | Bradley |
| 7,209,787 | B2 | 4/2007 | DiLorenzo |
| 2001/0031930 | A1 | 10/2001 | Roizen et al. |
| 2001/0037067 | A1 | 11/2001 | Tchou et al. |
| 2002/0077562 | A1 | 6/2002 | Kalgren et al. |
| 2002/0091308 | A1 | 7/2002 | Kipshidze et al. |
| 2002/0161412 | A1 | 10/2002 | Sun et al. |
| 2002/0169485 | A1 | 11/2002 | Pless et al. |
| 2002/0177882 | A1 | 11/2002 | DiLorenzo |
| 2002/0193697 | A1 | 12/2002 | Cho et al. |
| 2002/0193839 | A1 | 12/2002 | Cho et al. |
| 2003/0004423 | A1 | 1/2003 | Lavie et al. |
| 2003/0139692 | A1 | 7/2003 | Barrey et al. |
| 2003/0149457 | A1 | 8/2003 | Tcheng et al. |
| 2003/0153953 | A1 | 8/2003 | Park et al. |
| 2003/0153955 | A1 | 8/2003 | Park et al. |
| 2003/0153956 | A1 | 8/2003 | Park et al. |
| 2003/0163059 | A1 | 8/2003 | Poezevera et al. |
| 2003/0171791 | A1 | 9/2003 | KenKnight et al. |
| 2003/0195588 | A1 | 10/2003 | Fischell et al. |
| 2003/0212445 | A1 | 11/2003 | Weinberg |
| 2004/0002741 | A1 | 1/2004 | Weinberg |
| 2004/0002742 | A1 | 1/2004 | Florio |
| 2004/0015103 | A1 | 1/2004 | Aminian et al. |
| 2004/0049132 | A1 | 3/2004 | Barron et al. |
| 2004/0102814 | A1 | 5/2004 | Sorensen et al. |
| 2004/0111040 | A1 | 6/2004 | Ni et al. |
| 2004/0111041 | A1 | 6/2004 | Ni et al. |
| 2005/0021103 | A1 | 1/2005 | DiLorenzo |
| 2005/0021104 | A1 | 1/2005 | DiLorenzo |
| 2005/0042589 | A1 | 2/2005 | Hatlestad et al. |
| 2005/0113710 | A1 | 5/2005 | Stahmann et al. |
| 2005/0119703 | A1 | 6/2005 | DiLorenzo |
| 2005/0177192 | A1 | 8/2005 | Rezai et al. |
| 2005/0209511 | A1 | 9/2005 | Heruth et al. |
| 2005/0209512 | A1 | 9/2005 | Heruth et al. |
| 2005/0209513 | A1 | 9/2005 | Heruth et al. |
| 2005/0209643 | A1 | 9/2005 | Heruth et al. |
| 2005/0209644 | A1 | 9/2005 | Heruth et al. |
| 2005/0209645 | A1 | 9/2005 | Heruth et al. |
| 2005/0215847 | A1 | 9/2005 | Heruth et al. |
| 2005/0215947 | A1 | 9/2005 | Heruth et al. |
| 2005/0216064 | A1 | 9/2005 | Heruth et al. |
| 2005/0222522 | A1 | 10/2005 | Heruth et al. |
| 2005/0222626 | A1 | 10/2005 | DiLorenzo |
| 2005/0222643 | A1 | 10/2005 | Heruth et al. |
| 2005/0234514 | A1 | 10/2005 | Heruth et al. |
| 2005/0234518 | A1 | 10/2005 | Heruth et al. |
| 2005/0240086 | A1 | 10/2005 | Akay |
| 2005/0240242 | A1 | 10/2005 | DiLorenzo |
| 2005/0245790 | A1 | 11/2005 | Bergfalk et al. |
| 2005/0245988 | A1 | 11/2005 | Miesel |
| 2006/0224191 | A1 | 10/2006 | Dilorenzo |
| 2006/0293720 | A1 | 12/2006 | DiLorenzo |
| 2007/0073355 | A1 | 3/2007 | Dilorenzo |
| 2007/0142862 | A1 | 6/2007 | Dilorenzo |

FOREIGN PATENT DOCUMENTS

| | | |
|---|---|---|
| DE | 100 24 103 | 11/2001 |
| EP | 0 564 803 | 10/1993 |
| EP | 0 849 715 B1 | 6/1998 |
| EP | 1 195 139 | 4/2002 |
| EP | 1 195 139 A1 | 4/2002 |
| EP | 1 291 036 | 3/2003 |
| EP | 1 308 182 | 5/2003 |
| EP | 1 308 182 A2 | 5/2003 |
| EP | 1 437 159 | 7/2004 |
| EP | 1 437 159 A1 | 7/2004 |
| EP | 1 322 227 B1 | 12/2005 |
| GB | 2 330 912 | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |

WO WO 2005/035050 4/2005

OTHER PUBLICATIONS

M.T. Smith et al., "How do sleep disturbance and chronic pain interrelate? Insights from the longitudinal and cognitive-behavioral clinical trials literature," Sleep Medicine Reviews, YSMRV 286 pp. 1-14, Jun. 19, 2003.
Suanne Goodrich et al., "The Prediction of Pain Using Measures of Sleep Quality," Pain Digest (1998) 8:23-25.
"Analysis of heart rate dynamics by methods derived from nonlinear mathematics: Clinical applicability and prognostic significance" http:/herkules.oulu.fi.isbn9514250133/html/x222.html, 4 pgs. (downloaded 2004).
International Search Report and Written Opinion for corresponding PCT Application Serial No. PCT/US2005/008881, mailed Jul. 1, 2005 (10 pgs.).
"Watch," Wikipedia, the free encyclopedia, 6 pgs., http://en.wikipedia.org/wiki/Watch, (2006).
"IBM & Citizen Watch develop Linux-based 'WatchPad'," 5 pgs., http://www.linuxdevices.com/news/NS6580187845.html, (2006).
Tuisku, Katinka, "Motor Activity Measured by Actometry in Neuropsychiatric Disorders," Department of Psychiatry, University of Helsinski, Helsinki, Finland, 115 pgs., (2002).
Kassam, M., "2005 EDP Topic 'MK4': Tremor Data-Logger for Parkinson's Disease Patients," http://www.ee.ryerson.ca/~courses/edp2005/MK4.html, 3 pgs., (2006).
"Design Competition: Runners-Up for the Best Three Designs," EPN, vol. 26, No. 1, (2002).
"MiniMitter® Physiological and Behavioral Monitoring for Humans and Animals," http://www.minimitter.com/Products/Actiwatch, 3 pgs., (2006).
Notification of Transmittal of the International Preliminary Report on Patentability for PCT Application Serial No. PCT/US2005/008881, dated Mar. 7, 2006, 11 pgs.
Amzica, "Physiology of Sleep and Wakefulness as it Relates to the Physiology of Epilepsy," Journal of Clinical Neurophysiology, American Clinical Neurophysiology Society, 19(6), pp. 488-503, (2002).
Dinner, "Effect of Sleep on Epilepsy," Journal of Clinical Neurophysiology, American Clinical Neurophysiology Society, 19(6), pp. 504-513, (2002).
Foldvary-Schaefer, "Sleep Complaints and Epilepsy: the Role of Seizures, Antiepileptic Drugs and Sleep Disorders," Journal of Clinical Neurophysiology, American Clinical Neurophysiology Society, 19(6), pp. 514-521, (2002).
Mendez et al. "Interactions Between Sleep and Epilepsy," Journal of Clinical Neurophysiology, American Clinical Neurophysiology Society, 18(2), pp. 106-127, (2001).
Kerr et al., "Analysis of the sit-stand-sit movement cycle in normal subjects," Clinical Biomechanics, vol. 12, No. 4, pp. 236-245, (1997).
Aminian et al. "Physical Activity Monitoring Based on Accelerometry: Validation and Comparison with Video Observation," Medical & Biological Engineering & Computing, vol. 37, No. 2, pp. 304-308 (1999).
Medcare—A Global Leader in Sleep Diagnostics, Embletta Recording System, http://www.medcare.com/products/diagnostic/emblettata/, 2 pgs. Jan. 31, 2005.
Medcare—A Global Leader in Sleep Diagnostics, Somnologica for Embletta, http://www.medcare.com/products/diagnostic/embletta/SomnoEmbletta/index.asp, 1 pg. Jan. 31, 2005.
MAP Medizin-Technologie GmbH, Poly-MESAM®, http://195.244.124.130/map/de/eng/map_med.nsf/cmsa11/70564A3FCBE4188AC1256EF4.., 4 pgs. Jan. 31, 2005.
Merlin, http://www.aha.ru/~pir/english/merlin/, 4 pgs. Jan. 31, 2005.
Sleep Solutions—PR Newswire: Sleep Solutions Introduces NovaSom™ QSG™ for PSG.., http://www.sleep-solutions.com/press_room/novasom.htm, 2 pgs. Jan. 31, 2005.
Itamar Medical Information, http://itamar-medical.com/content.asp?id-id=31, 2 pgs. Jan. 31, 2005.
Criticare System Inc.,-504DX Portable Pulse Oximeter, http://www.csiusa.com/504dx.html, 4 pgs. Jan. 31, 2005.
Snap® Laboratories, Product Fact Sheet, http://www.snaplab.com/mp_fact.htm, 2 pgs. Jan. 31, 2005.
Sleep Strip & Bite Strip, http://www.quietsleep.com/snoringapnea/sleepstrip.htm, 8 pgs. Jan. 31, 2005
"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.
"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.
"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.
Office Action dated May 5, 2008 for U.S. Appl. No. 10/826,925 (12 pgs.).
Office Action dated May 30, 2008 for U.S. Appl. No. 11/081,811 (13 pgs.).
Office Action dated May 6, 2008 for U.S. Appl. No. 10/825,955 (13 pgs.).
Response to Office Action dated Jul. 2, 2008 for U.S. Appl. No. 10/825,955 (13 pgs.).
Office Action dated May 9, 2008 for U.S. Appl. No. 11/081,857 (10 pgs.).
Responsive Amendment dated Aug. 7, 2008 for U.S. Appl. No. 11/081,857 (13 pgs.).
Response dated Aug. 22, 2008 for U.S. Appl. No. 10/826,925 (7 pgs.).
Responsive Amendment dated Aug. 29, 2008 for U.S. Appl. No. 11/081,811 (13 pgs.).
Office Action dated Sep. 5, 2008 for U.S. Appl. No. 10/825,964 (6 pgs.).
Responsive Amendment dated Jan. 5, 2009 for U.S. Appl. No. 10/825,964 (13 pgs.).
Office Action dated Nov. 6, 2008 for U.S. Appl. No. 11/081,857 (8 pgs.).
Response dated Jan. 6, 2009 for U.S. Appl. No. 11/081,857 (6 pgs.).
Office Action dated Dec. 12, 2008 for U.S. Appl. No. 11/081,811 (12 pgs.).
Responsive Amendment dated Mar. 12, 2009 for U.S. Appl. No. 11/081,811 (13 pgs.).
Sazonov et al., "Activity-based sleep-wake identification in infants," Institute of Physics Publishing, Physiological Measurement, 25, pp. 1291-1304, Aug. 11, 2004.
Office Action dated Oct. 14, 2009 for U.S. Appl. No. 11/081,857 (14 pgs.).
Response dated Dec. 14, 2009 for U.S. Appl. No. 11/081,857 (8 pgs.).
Advisory Action dated Jan. 12, 2010 for U.S. Appl. No. 11/081,857 (3 pgs.).
Responsive Amendment dated Mar. 22, 2010 for Appl. No. 11/691,405 (18 pgs.).
Office Action dated Dec. 21, 2009 for U.S. Appl. No. 11/691,405 (11 pgs.).
Office Action dated Mar. 12, 2010 for U.S. Appl. No. 11/691,413 (7 pgs.).
Office Action dated May 19, 2010 for U.S. Appl. No. 11/691,405 (12 pgs.).
Office Action dated May 20, 2010 for U.S. Appl. No. 12/248,622 (6 pgs.).
Responsive Amendment dated Jun. 9, 2010 for U.S. Appl. No. 11/691,413 (16 pgs.).
Responsive Amendment dated Jun. 2, 2010 for U.S. Appl. No. 11/691,430 (15 pgs.).
Final Office Action for U.S. Appl. No. 11/081,811, mailed Apr. 28, 2010, 15 pages.
Responsive Amendment to Final Office Action for U.S. Appl. No. 11/081,811, filed Jun. 28, 2010, 18 pages.

* cited by examiner

DETECTING SLEEP

This application is a continuation-in-part of U.S. patent application Ser. No. 10/825,964, filed Apr. 15, 2004, which claims the benefit of U.S. Provisional Application No. 60/553,771, filed Mar. 16, 2004. The entire content of both applications is incorporated herein by reference.

TECHNICAL FIELD

The invention relates to medical devices, and to techniques for determining whether a patient is asleep.

BACKGROUND

The ability to determine whether a patient is asleep is useful in a variety of medical contexts. In some situations, the ability to determine whether a patient is asleep is used to diagnose conditions of the patient. For example, the amount of time that patients sleep, the extent of arousals during sleep, and the times of day that patients sleep have been used to diagnose sleep apnea. Such sleep information could also be used to diagnose psychological disorders, such as depression and mania.

In other situations, a determination as to whether a patient is asleep is used to control delivery of therapy to the patient. For example, neurostimulation or drug therapies can be suspended when the patient is asleep, or the intensity/dosage of the therapies can be reduced when a patient is asleep. As another example, the rate response settings of a cardiac pacemaker may be adjusted to less aggressive settings when the patient is asleep so that the patient's heart will not be paced at an inappropriately high rate during sleep. In these examples, therapy may be suspended or adjusted when the patient is asleep to avoid patient discomfort, or to conserve a battery and/or contents of a fluid reservoir of an implantable medical device when the therapy may be unneeded or ineffective. However, in other cases, a therapy intended to be delivered when the patient is asleep, such as therapy intended to prevent or treat sleep apnea, is delivered based on a determination that the patient is asleep.

Existing techniques for determining whether a patient is asleep include monitoring the electroencephalogram (EEG) of the patient to identify brain wave activity indicative of sleep. However, EEG monitoring typically requires that an array of electrodes be placed on a patient's scalp and coupled to an external monitoring device, and is most often performed in a clinic setting. Generally, an implantable medical device may only be used to monitor a patient's EEG in the rare cases when it is coupled to electrodes implanted within the brain of the patient. Consequently, existing EEG monitoring techniques are generally unsuitable for determining whether a patient is asleep in order to control therapy, or for long-term monitoring of the patient's sleep/wake cycle.

Existing techniques employed by implantable medical devices to determine whether a patient is asleep include monitoring the patient's respiration rate, respiration rate variability, and activity level. Each of these physiological parameters may be an inaccurate indicator of whether a patient is asleep. For example, from the perspective of these physiological parameters, it may appear that a patient is sleeping when, instead, the patient is merely lying down in a relaxed state. As another example, respiration rate and respiration rate variability, for example, may fail to accurately indicate that the patient is asleep when the patient suffers from a breathing disorder, such as Cheyne-Stokes syndrome.

SUMMARY

In general, the invention is directed to techniques for determining whether a patient is asleep. In some embodiments, the invention is directed to techniques that involve determination of values of one or more sleep metrics that indicate a probability of a patient being asleep based on the current value of one or more physiological parameters of the patient. Use of a plurality of sleep metrics, in particular, may allow for a more accurate determination of whether a patient is asleep.

A system according to the invention includes one or more sensors and a processor. Each of the sensors generates a signal as a function of at least one physiological parameter of a patient that may discernibly change when the patient is asleep. Exemplary physiological parameters include activity level, posture, heart rate, electrocardiogram (ECG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response.

The processor monitors the physiological parameters based on the signals generated by the sensors, and determines whether the patient is asleep based on values for the physiological parameters. The value for a physiological parameter may be a current, mean or median value for the parameter. In some embodiments, the processor may additionally or alternatively determine whether the patient is asleep based on the variability of one or more of the physiological parameters.

In some embodiments, the processor determines a value of a sleep metric that indicates a probability of the patient being asleep based on a physiological parameter. In particular, the processor may apply a function or look-up table to the current value and/or variability of the physiological parameter to determine the sleep metric value. The processor may compare the sleep metric value to a threshold value to determine whether the patient is asleep. In some embodiments, the processor may compare the sleep metric value to each of a plurality of thresholds to determine the current sleep state of the patient, e.g., rapid eye movement (REM), or one of the nonrapid eye movement (NREM) states (S1, S2, S3, S4). Because they provide the most "refreshing" type of sleep, the ability to determine whether the patient is in one of the S3 and S4 sleep states may be, in some embodiments, particularly useful.

Further, in some embodiments the processor may determine a sleep metric value for each of a plurality of physiological parameters. In other words, the processor may apply a function or look-up table for each parameter to the current value for that parameter in order to determine the sleep metric value for that parameter. The processor may average or otherwise combine the plurality of sleep metric values to provide an overall sleep metric value for comparison to the threshold values. In some embodiments, a weighting factor may be applied to one or more of the sleep metric values. One or more of functions, look-up tables, thresholds and weighting factors may be selected or adjusted by a user in order to select or adjust the sensitivity and specificity of the system in determining whether the patient is asleep.

In some embodiments, the processor is included as part of a medical device, such as an implantable medical device. The sensors may also be included within the medical device, coupled to the medical device by one or more leads, or in wireless communication with the medical device. The medical device may control delivery of therapy to the patient based on the determination as to whether the patient is asleep, or may store information indicating when the patient is asleep for later retrieval and analysis by user. In some embodiments, the medical device may instead use the one or more sleep metric values to control delivery of therapy, or may store one or more sleep metric values. In some embodiments, information relating to the patient's sleep patterns may be used to diagnose sleep or psychological disorder, or may be used to evaluate the effectiveness of a therapy delivered to the patient.

In one embodiment, the invention is directed to a method in which a plurality of physiological parameters of a patient are monitored and a value of a sleep metric that indicates a probability of the patient being asleep is determined based on the physiological parameters. The physiological parameters may comprise at least one of electrocardiogram morphology, core temperature, or subcutaneous temperature, muscular tone, brain electrical activity, or eye motion.

In another embodiment, the invention is directed to a medical system that comprises a plurality of sensors and a processor. Each of the sensors generate a signal as a function of at least one physiological parameter of a patient. The processor monitors a plurality of physiological parameters of the patient based on the signals output by the sensors, and determines a value of a sleep metric that indicates a probability of the patient being asleep based on the physiological parameters. The physiological parameters may comprise at least one of electrocardiogram morphology, core temperature, or subcutaneous temperature, muscular tone, brain electrical activity, or eye motion.

In another embodiment, the invention is directed to a medical system that comprises means for monitoring a plurality of physiological parameters of a patient and means for determining a value of a sleep metric that indicates a probability of the patient being asleep based on the physiological parameters. The physiological parameters may comprise at least one of electrocardiogram morphology, core temperature, or subcutaneous temperature, muscular tone, brain electrical activity, or eye motion.

In another embodiment, the invention is directed to a computer-readable medium comprising program instructions. The instructions cause a programmable processor to monitor a plurality of physiological parameters of a patient, and determine a value of a sleep metric that indicates a probability of the patient being asleep based on the physiological parameters. The physiological parameters may comprise at least one of electrocardiogram morphology, core temperature, or subcutaneous temperature, muscular tone, brain electrical activity, or eye motion.

The invention may be capable of providing one or more advantages. For example, the invention provides techniques for determining a sleep state of a patient that may be implemented in an implantable medical device. Further, the techniques provided by the invention may include analysis of a variety of physiological parameters not previously used in determining whether a patient is asleep. Where it is desired to detect sleep via an implantable medical device, the ability to determine whether a patient is sleeping based on these physiological parameters may increase the number of implantable medical device types in which the invention may be implemented, i.e., the invention may be implemented in a variety of types of implantable medical devices which include or may be easily modified to include sensors capable of generating a signal based on such physiological parameters.

Monitoring a plurality of physiological parameters according to some embodiments, rather than a single parameter, may allow for a more accurate determination of whether a patient is asleep than is available via existing implantable medical devices. Use of sleep metrics that indicate a probability of the patient being asleep for each of a plurality of physiological parameters may further increase the reliability with which an implantable medical device may determine whether a patient is asleep. In particular, rather than a binary sleep or awake determination for each of a plurality of parameters, sleep metric values for each of a plurality of parameters may be combined to yield an overall sleep metric value that may be compared to a threshold to determine whether the patient is asleep. In other words, failure of any one physiological parameter to accurately indicate whether a patient is sleeping may be less likely to prevent the implantable medical device from accurately indicating whether the patient is sleeping when considered in combination with other physiological parameters.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
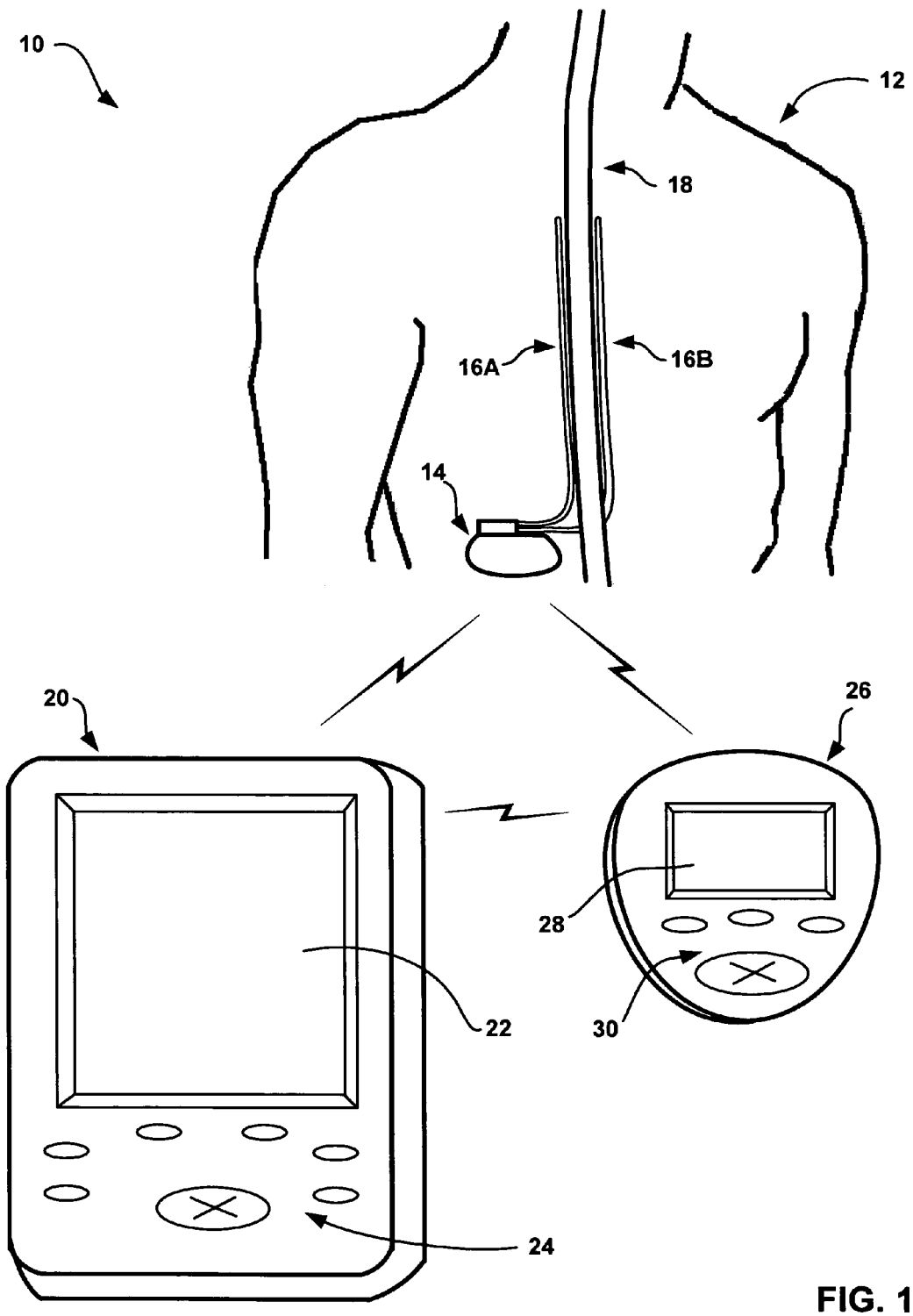
FIG. 1 is a conceptual diagram illustrating an example system including an implantable medical device that determines whether a patient is asleep according to the invention.

FIG. 1 is a conceptual diagram illustrating an example system 10 that includes an implantable medical device (IMD) 14 that determines whether a patient 12 is asleep according to the invention. In the illustrated example system, IMD 14 takes the form of an implantable neurostimulator that delivers neurostimulation therapy in the form of electrical pulses to patient 12. However, the invention is not limited to implementation via an implantable neurostimulator, or even to implementation via an IMD.

For example, in some embodiments of the invention, an implantable pump or implantable cardiac pacemaker may determine whether a patient is asleep. In other embodiments, the medical device that determines when patient 12 is asleep may be an implantable or external patient monitor. Further, a programming device or other computing device may determine when patient 12 is asleep based on information collected by a medical device. In other words, any implantable or external device may determine whether a patient is asleep according to the invention.

In the illustrated example, IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis.

IMD 14 delivers therapy according to a set of therapy parameters that define the delivered therapy. In embodiments where IMD 14 delivers neurostimulation therapy in the form of electrical pulses, the parameters for each of the parameter sets may include voltage or current pulse amplitudes, pulse widths, pulse rates, and the like. Further, each of leads 16 includes electrodes (not shown in FIG. 1), and the parameters may include information identifying which electrodes have been selected for delivery of pulses, and the polarities of the selected electrodes.

System 10 also includes a clinician programmer 20. A clinician (not shown) may use clinician programmer 20 to program neurostimulation therapy for patient 12. Clinician programmer 20 may, as shown in FIG. 1, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus, mouse, or the like. Keypad 24 may take the form of an alphanumeric keypad or a reduced set of keys associated with particular functions.

System 10 also includes a patient programmer 26, which also may, as shown in FIG. 1, be a handheld computing device. Patient 12 may use patient programmer 26 to control the delivery of neurostimulation therapy by IMD 14. Patient programmer 26 may also include a display 28 and a keypad 30, to allow patient 12 to interact with patient programmer 26. In some embodiments, display 28 may be a touch screen display, and patient 12 may interact with patient programmer 26 via display 28. Patient 12 may also interact with patient programmer 26 using peripheral pointing devices, such as a stylus or mouse.

IMD 14, clinician programmer 20 and patient programmer 26 may, as shown in FIG. 1, communicate via wireless communication. Clinician programmer 20 and patient programmer 26 may, for example, communicate via wireless communication with IMD 14 using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMD 14 is capable of determining whether patient 12 is asleep. Specifically, as will be described in greater detail below, IMD 14 monitors a plurality of physiological parameters of patient 12 that may discernibly change when patient 12 is asleep, and determines whether patient 12 is asleep based on values of the physiological parameters. The value for a physiological parameter may be a current, mean or median value for the parameter. In some embodiments, IMD 14 may additionally or alternatively determine whether patient 12 is asleep based on the variability of one or more of the physiological parameters. IMD 14 includes, is coupled to, or is in wireless communication with one or more sensors, and monitors the physiological parameters via the sensors.

Exemplary physiological parameters that may be monitored by IMD 14 include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. In some external medical device embodiments of the invention, galvanic skin response may additionally or alternatively be monitored. Some of the parameters, such as activity level, heart rate, some ECG morphological features, respiration rate, respiratory volume, blood pressure, arterial oxygen saturation and partial pressure, partial pressure of oxygen in the cerebrospinal fluid, muscular activity and tone, core temperature, subcutaneous temperature, arterial blood flow, and galvanic skin response may be at low values when patient 12 is asleep. Further, the variability of at least some of these parameters, such as heart rate and respiration rate, may be at a low value when the patient is asleep. Information regarding the posture of patient 12 will most likely indicate that patient 12 is lying down when patient 12 is asleep.

In some embodiments, IMD 14 determines a value of one or more sleep metrics based on a value of one or more physiological parameters of patient 12. A sleep metric value may be a numeric value that indicates the probability that patient 12 is asleep. In some embodiments, the sleep metric value may be a probability value, e.g., a number within the range from 0 to 1.

In particular, the IMD 14 may apply a function or look-up table to the current, mean or median value, and/or the variability of the physiological parameter to determine a value of the sleep metric. IMD 14 may compare the sleep metric value to a threshold value to determine whether the patient is asleep. In some embodiments, the IMD 14 may compare the sleep metric value to each of a plurality of thresholds to determine the current sleep state of the patient, e.g., rapid eye movement (REM), S1, S2, S3, or S4. Because they provide the most "refreshing" type of sleep, the ability to determine whether the patient is in one of the S3 and S4 sleep states may be, in some embodiments, particularly useful.

Further, in some embodiments IMD 14 may determine a sleep metric value for each of a plurality of physiological parameters. In other words, IMD 14 may apply a function or look-up table for each parameter to a value for that parameter in order to determine the sleep metric value for that parameter. IMD 14 may average or otherwise combine the plurality of sleep metric values to provide an overall sleep metric value for comparison to the threshold values. In some embodiments, IMD 14 may apply a weighting factor to one or more of the sleep metric values prior to combination. One or more of functions, look-up tables, thresholds and weighting factors may be selected or adjusted by a user, such as a clinician via programmer 20 or patient 12 via programmer 26, in order to select or adjust the sensitivity and specificity of IMD 14 in determining whether patient 12 is asleep.

Monitoring a plurality of physiological parameters according to some embodiments, rather than a single parameter, may allow IMD 14 to determine whether patient 12 is asleep with more accuracy than existing implantable medical devices. Use of sleep metric values that indicate a probability of the patient being asleep for each of a plurality of physiological parameters may further increase the accuracy with which IMD 14 may determine whether patient 12 is asleep. In particular, rather than a binary sleep or awake determination for each of a plurality of parameters, sleep metric values for each of a plurality of parameters may be combined to yield an overall sleep metric value that may be compared to a threshold to determine whether patient 12 is asleep. In other words, failure of any one physiological parameter to accurately indicate whether a patient is sleeping may be less likely to prevent IMD 14 from accurately indicating whether patient 12 is sleeping when considered in combination with other physiological parameters.

IMD 14 may control delivery of therapy to patient 12 based on the determination as to whether patient 12 is asleep. For example, IMD 14 may suspend delivery of neurostimulation or reduce the intensity of delivered neurostimulation when patient 14 is determined to be asleep. In other embodiments, IMD 14 may suspend or reduce intensity of drug delivery, or may reduce the aggressiveness of rate response for cardiac pacing when patient 12 is determined to be asleep. In still other embodiments, IMD 14 may initiate delivery of a therapy, such as a therapy to treat or prevent sleep apnea, when patient 12 is determined to be asleep.

In some embodiments, IMD 14 stores information indicating when patient 12 is asleep, which may be retrieved for analysis by a clinician via programmer 20, for example. The clinician may use the sleep information to diagnose conditions of patient 12, such as sleep apnea or psychological disorders. Information relating to the sleep patterns of patient 12 may in other situations indicate the effectiveness of a delivered therapy and/or the need for increased therapy. Some ailments of patient 12, such as chronic pain, tremor, gastrointestinal disorders, incontinence, congestive heart failure, and sleep apnea may disturb or hinder the sleep or patient 12, or, in some cases, inadequate or disturbed sleep may increase the symptoms of these ailments.

IMD 14 may collect information relating to the sleep patterns of patient 12, which may be retrieved by a clinician via programmer 20 and used to evaluate the effectiveness of a therapy delivered to patient 12 for such an ailment, or to indicate the need for an additional therapy to improve the sleep pattern of patient 12. In some cases, IMD 14 may evaluate such collected sleep information and automatically adjust a therapy for such a condition based on the evaluation. Further information regarding evaluation of a therapy based on sleep information collected by an IMD may be found in a commonly-assigned and copending U.S. patent application Ser. No. 11/081,811 by Ken Heruth and Keith Miesel, entitled "COLLECTING SLEEP QUALITY INFORMATION VIA A MEDICAL DEVICE," which is filed on Mar. 16, 2005. Further information regarding automatic control of a therapy based on sleep information collected by an IMD may be found in a commonly-assigned and copending U.S. patent application Ser. No. 11/081,155 by Ken Heruth and Keith Miesel, entitled "CONTROLLING THERAPY BASED ON SLEEP QUALITY," which is filed on Mar. 16, 2005. The entire content of both of these applications is incorporated herein by reference.

Figure 2:
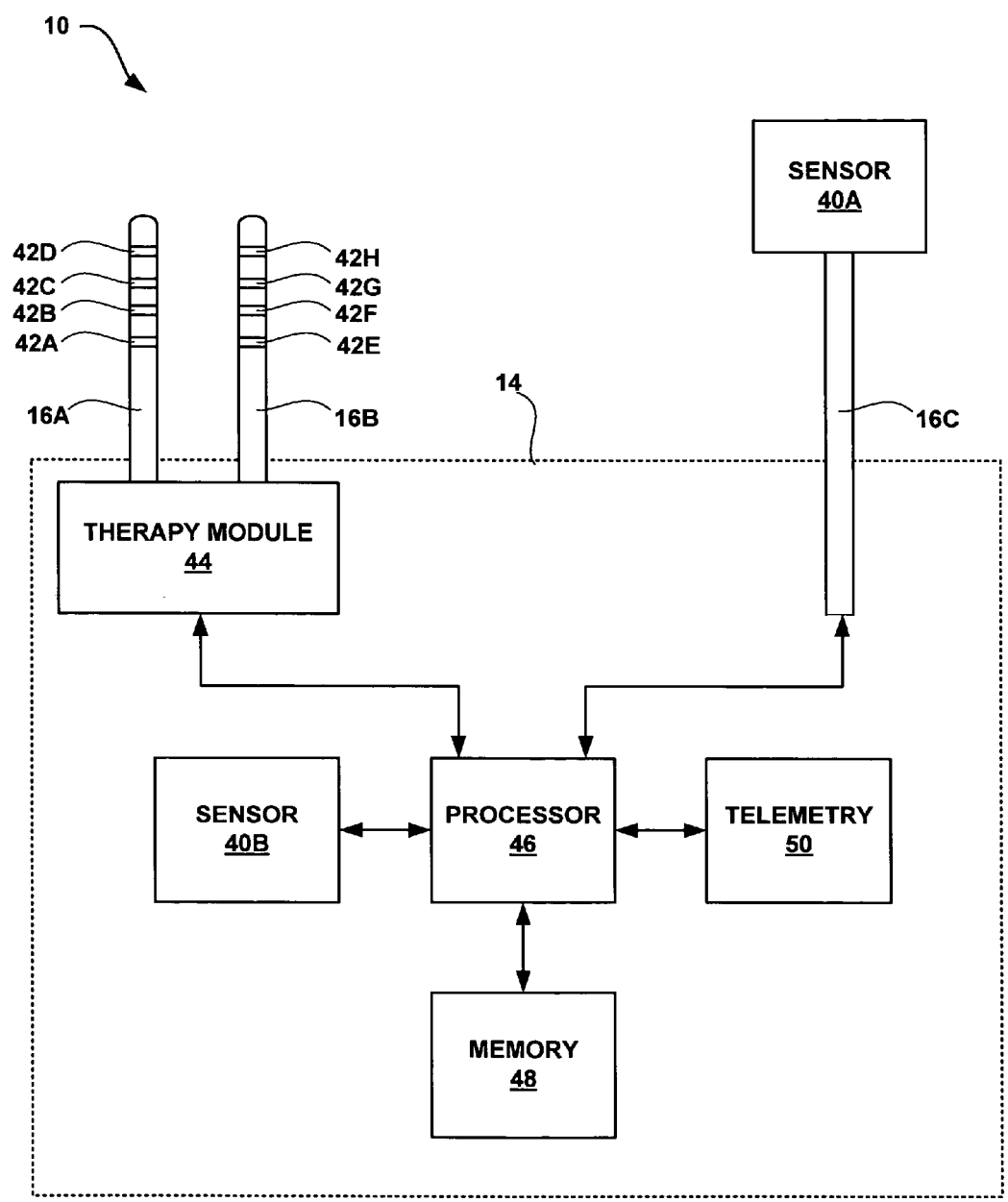
FIG. 2 is a block diagram further illustrating the system of FIG. 1

FIG. 2 is a block diagram further illustrating system 10. In particular, FIG. 2 illustrates an example configuration of IMD 14 and leads 16A and 16B. FIG. 2 also illustrates sensors 40A and 40B (collectively "sensors 40") that generate signals as a function of one or more physiological parameters of patient 12. IMD 14 monitors the signals to determine whether patient 12 is asleep.

IMD 14 may deliver neurostimulation therapy via electrodes 42A-D of lead 16A and electrodes 42E-H of lead 16B (collectively "electrodes 42"). Electrodes 42 may be ring electrodes. The configuration, type and number of electrodes 42 illustrated in FIG. 2 are merely exemplary. For example, leads 16A and 16B may each include eight electrodes 42, and the electrodes 42 need not be arranged linearly on each of leads 16A and 16B.

Electrodes 42 are electrically coupled to a therapy delivery module 44 via leads 16A and 16B. Therapy delivery module 44 may, for example, include a pulse generator coupled to a power source such as a battery. Therapy delivery module 44 may deliver electrical pulses to patient 12 via at least some of electrodes 42 under the control of a processor 46, which controls therapy delivery module 44 to deliver neurostimulation therapy according to a set of therapy parameters, which may be one of a plurality of therapy parameter sets stored in memory 48. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal as a function of one or more physiological parameters of patient 12. Although shown as including two sensors 40, system 10 may include any number of sensors. As illustrated in FIG. 2, sensors 40 may be included as part of IMD 14, or coupled to IMD 14 via leads 16. Sensors 40 may be coupled to IMD 14 via therapy leads 16A and 16B, or via other leads 16, such as lead 16C depicted in FIG. 2. In some embodiments, a sensor located outside of IMD 14 may be in wireless communication with processor 46. Wireless communication between sensors 40 and IMD 14 may, as examples, include RF communication or communication via electrical signals conducted through the tissue and/or fluid of patient 12.

As discussed above, exemplary physiological parameters of patient 12 that may be monitored by IMD 14 to determine values of one or more sleep metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. Further, as discussed above, in some external medical device embodiments of the invention galvanic skin response may additionally or alternatively be monitored. The detected values of these physiological parameters of patient 12 may discernibly change when patient 12 falls asleep or wakes up. Some of these physiological parameters may be at low values when patient 12 is asleep. Further, the variability of at least some of these parameters, such as heart rate and respiration rate, may be at a low value when the patient is asleep. Sensors 40 may be of any type known in the art capable of generating a signal as a function of one or more of these parameters.

For example, sensors 40 may include electrodes located on leads or integrated as part of the housing of IMD 14 that generate an electrogram signal as a function of electrical activity of the heart of patient 12, and processor 46 may monitor the heart rate of patient 12 based on the electrogram signal. In other embodiments, a sensor may include an acoustic sensor within IMD 14, a pressure or flow sensor within the bloodstream or cerebrospinal fluid of patient 12, or a temperature sensor located within the bloodstream of patient 12. The signals generated by such sensors may vary as a function of contraction of the heart of patient 12, and can be used by IMD 14 to monitor the heart rate of patient 12.

In some embodiments, processor 46 may detect, and measure values for one or more ECG morphological features within an electrogram generated by electrodes as described above. ECG morphological features may vary in a manner that indicates whether patient 12 is asleep or awake. For example, the amplitude of the ST segment of the ECG may decrease when patient 12 is asleep. Further, the amplitude of QRS complex or T-wave may decrease, and the widths of the QRS complex and T-wave may increase when patient 12 is asleep. The QT interval and the latency of an evoked response may increase when patient 12 is asleep, and the amplitude of the evoked response may decrease when patient 12 is asleep.

Sensors 40 may include one or more accelerometers, gyros, mercury switches, or bonded piezoelectric crystals that generate a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of patient 12 to detect muscle activity associated with walking, running or the like. The electrodes may be coupled to IMD 14 wirelessly or by leads 16 or, if IMD 14 is implanted in these locations, integrated with a housing of IMD 14.

However, bonded piezoelectric crystals located in these areas generate signals as a function of muscle contraction in addition to body motion, footfalls or other impact events. Consequently, use of bonded piezoelectric crystals to detect activity of patient 12 may be preferred in some embodiments in which it is desired to detect muscle activity in addition to body motion, footfalls, or other impact events. Bonded piezoelectric crystals may be coupled to IMD 14 wirelessly or via leads 16, or piezoelectric crystals may be bonded to the can of IMD 14 when the IMD is implanted in these areas, e.g., in the back, buttocks, chest, or abdomen of patient 12.

Processor 46 may detect spasmodic or pain related muscle activation via the signals generated by electrodes or a bonded piezoelectric crystal in addition to the electrical activation and contractions of muscles associated with gross motor activity of the patient, e.g., walking, running or the like. Spasmodic or pain related muscle activation may indicate that patient 12 is not sleeping, e.g., unable to sleep.

Sensors 40 may also include a plurality of accelerometers, gyros, or magnetometers oriented orthogonally that generate signals that indicate the posture of patient 12. In addition to being oriented orthogonally with respect to each other, each of sensors 40 used to detect the posture of patient 12 may be generally aligned with an axis of the body of patient 12. When accelerometers, for example, are aligned in this manner, the magnitude and polarity of DC components of the signals generate by the accelerometers indicate the orientation of the patient relative to the Earth's gravity, e.g., the posture of patient 12. Further information regarding use of orthogonally aligned accelerometers to determine patient posture may be found in a commonly-assigned U.S. Pat. No. 5,593,431, which issued to Todd J. Sheldon.

Other sensors 40 that may generate a signal that indicates the posture of patient 12 include electrodes that generate an electromyogram (EMG) signal, or bonded piezoelectric crystals that generate a signal as a function of contraction of muscles. Such sensors 40 may be implanted in the legs, buttocks, chest, abdomen, or back of patient 12, as described above. The signals generated by such sensors when implanted in these locations may vary based on the posture of patient 12, e.g., may vary based on whether the patient is standing, sitting, or laying down.

Further, the posture of patient 12 may affect the thoracic impedance of the patient. Consequently, sensors 40 may include an electrode pair, including one electrode integrated with the housing of IMD 14 and one of electrodes 42, that generates a signal as a function of the thoracic impedance of patient 12, and processor 46 may detect the posture or posture changes of patient 12 based on the signal. The electrodes of the pair may be located on opposite sides of the patient's thorax. For example, the electrode pair may include one of electrodes 42 located proximate to the spine of a patient for delivery of SCS therapy, and IMD 14 with an electrode integrated in its housing may be implanted in the abdomen of patient 12.

Additionally, changes of the posture of patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMD 14 wirelessly or via lead 16. CSF pressure changes associated with posture changes may be particularly evident within the brain of the patient, e.g., may be particularly apparent in an intracranial pressure (ICP) waveform.

The thoracic impedance of patient 12 may also vary based on the respiration of patient 12. Consequently, in some embodiments, an electrode pair that generates a signal as a function of the thoracic impedance of patient 12 may be used to detect respiration of patient 12. In other embodiments, sensors 40 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 40 may include electrodes that generate an electromyogram (EMG) signal as a function of muscle electrical activity, as described above, or may include any of a variety of known temperature sensors to generate a signal as a function of a core subcutaneous temperature of patient 12. Such electrodes and temperature sensors may be incorporated within the housing of IMD 14, or coupled to IMD 14 wirelessly or via leads. Sensors 40 may also include a pressure sensor within, or in contact with, a blood vessel. The pressure sensor may generate a signal as a function of the a blood pressure of patient 12, and may, for example, comprise a Chronicle Hemodynamic Monitor™ commercially available from Medtronic, Inc. of Minneapolis, Minn. Further, certain muscles of patient 12, such as the muscles of the patient's neck, may discernibly relax when patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of IMD 14, which generate signals as a function of blood oxygen saturation and blood oxygen partial pressure respectively. In some embodiments, system 10 may include a catheter with a distal portion located within the cerebrospinal fluid of patient 12, and the distal end may include a Clark sensor to generate a signal as a function of the partial pressure of oxygen within the cerebrospinal fluid. Embodiments in which an IMD comprises an implantable pump, for example, may include a catheter with a distal portion located in the CSF.

In some embodiments, sensors 40 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of patient 12 to generate a signal as a function of galvanic skin response.

Additionally, in some embodiments, sensors 40 may include one or more electrodes positioned within or proximate to the brain of patient, which detect electrical activity of the brain. For example, in embodiments in which IMD 14 delivers stimulation or other therapy to the brain, processor 46 may be coupled to electrodes implanted on or within the brain via a lead 16. In other embodiments, processor 46 may be wirelessly coupled to electrodes that detect brain electrical activity.

For example, one or more modules may be implanted beneath the scalp of the patient, each module including a housing, one or more electrodes, and circuitry to wirelessly transmit the signals detected by the one or more electrodes to IMD 14. In other embodiments, the electrodes may be applied to the patient's scalp, and electrically coupled to a module that includes circuitry for wirelessly transmitting the signals detected by the electrodes to IMD 14. The electrodes may be glued to the patient's scalp, or a head band, hair net, cap, or the like may incorporate the electrodes and the module, and may be worn by patient 12 to apply the electrodes to the patient's scalp when, for example, the patient is attempting to sleep. The signals detected by the electrodes and transmitted to IMD 14 may be electroencephalogram (EEG) signals, and processor 46 may identify the amplitude and or frequency of the EEG signals as physiological parameter values.

Also, the motion of the eyes of patient 12 may vary depending on whether the patient is sleeping and which sleep state the patient is in. Consequently, sensors 40 may include electrodes place proximate to the eyes of patient 12 to detect electrical activity associated with motion of the eyes, e.g., to generate an electro-oculography (EOG) signal. Such electrodes may be coupled to IMD 14 via one or more leads 16, or may be included within modules that include circuitry to wirelessly transmit detected signals to IMD 14. Wirelessly coupled modules incorporating electrodes to detect eye motion may be worn externally by patient 12, e.g., attached to the skin of patient 12 proximate to the eyes by an adhesive when the patient is attempting to sleep.

Processor 46 monitors the physiological parameters based on the signals generated by the one or more sensors 40, and determines whether patient 12 is asleep based on current values for the physiological parameters. In some embodiments, processor 46 may determine mean or median value for the parameter based on values of the signal over time, and determines whether patient 12 is asleep based on the mean or median value. In other embodiments, processor 46 may additionally or alternatively determine a variability of one or more of the parameters based on the values of the parameter over time, and may determine whether patient 12 is asleep based on the one or more variability values. IMD 14 may include circuitry (not shown) that conditions the signals generate by sensors 40 such that they may be analyzed by processor 46. For example, IMD 14 may include one or more analog to digital converters to convert analog signals generate by sensors 40 into digital signals usable by processor 46, as well as suitable filter and amplifier circuitry.

In some embodiments, processor 46 determines a value of a sleep metric that indicates a probability of the patient being asleep based on a physiological parameter. In particular, processor 46 may apply a function or look-up table to the current value, mean or median value, and/or variability of the physiological parameter to determine the sleep metric value. For example, the values of one or more physiological parameters serve as indices to the lookup table to yield a corresponding output value, which serves as the sleep metric value. Processor 46 may compare the sleep metric value to a threshold value to determine whether patient 12 is asleep. In some embodiments, processor 46 may compare the sleep metric value to each of a plurality of thresholds to determine the current sleep state of patient 12, e.g., rapid eye movement (REM), S1, S2, S3, or S4.

Further, in some embodiments processor 46 determines a sleep metric value for each of a plurality of monitored physiological parameters. In other words, processor 46 may apply a function or look-up table for each parameter to the current value for that parameter in order to determine the sleep metric value for that individual parameter. Processor 46 may then average or otherwise combine the plurality of sleep metric values to provide an overall sleep metric value, and may determine whether patient 12 is asleep based on the overall sleep metric value. In some embodiments, processor 46 may apply a weighting factor to one or more of the sleep metric values prior to combination.

Figure 3:
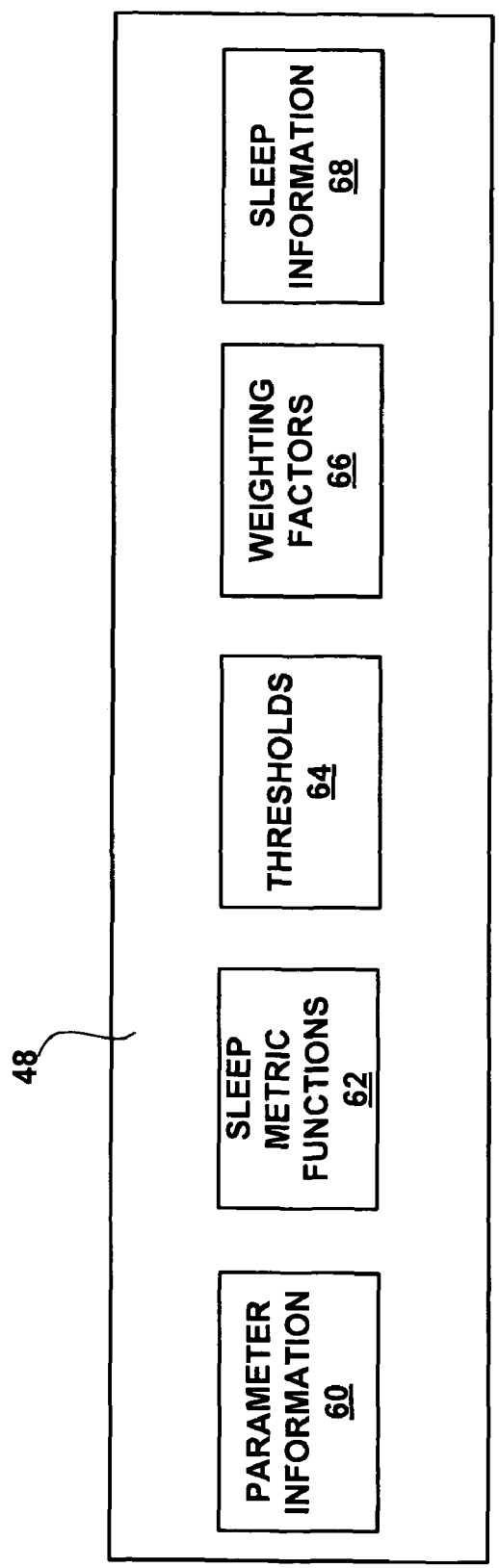
FIG. 3 is a block diagram illustrating a memory within an implantable medical device of the system of FIG. 1.

As shown in FIG. 3, memory 48 may include parameter information 60 recorded by processor 46, e.g., parameter values, or mean or median parameter values. Memory 48 may also store sleep metric functions 62 or look-up tables (not shown) that processor 46 may retrieve for application to physiological parameter values or variability values, and threshold values 64 that processor 46 may use to determine whether patient 12 is asleep and, in some embodiments, the sleep state of patient 12. Memory 48 may also store weighting factors 66 used by processor 46 when combining sleep metric values to determine an overall sleep metric value. Processor 46 may store sleep information 68 within memory 48, such as recorded sleep metric values and information indicating when patient 12 was asleep.

As shown in FIG. 2, IMD 14 also includes a telemetry circuit 50 that allows processor 46 to communicate with clinician programmer 20 and patient programmer 26. For example, using clinician programmer 20, a clinician may direct processor 46 to retrieve sleep information 68 from memory 48 and transmit the information via telemetry circuit 50 to programmer 20 for analysis. Further, the clinician may select or adjust the one or more of functions 62, look-up tables, thresholds 64 and weighting factors 66 in order to select or adjust the sensitivity and specificity of processor 46 determining whether the patient is asleep.

Figure 4:
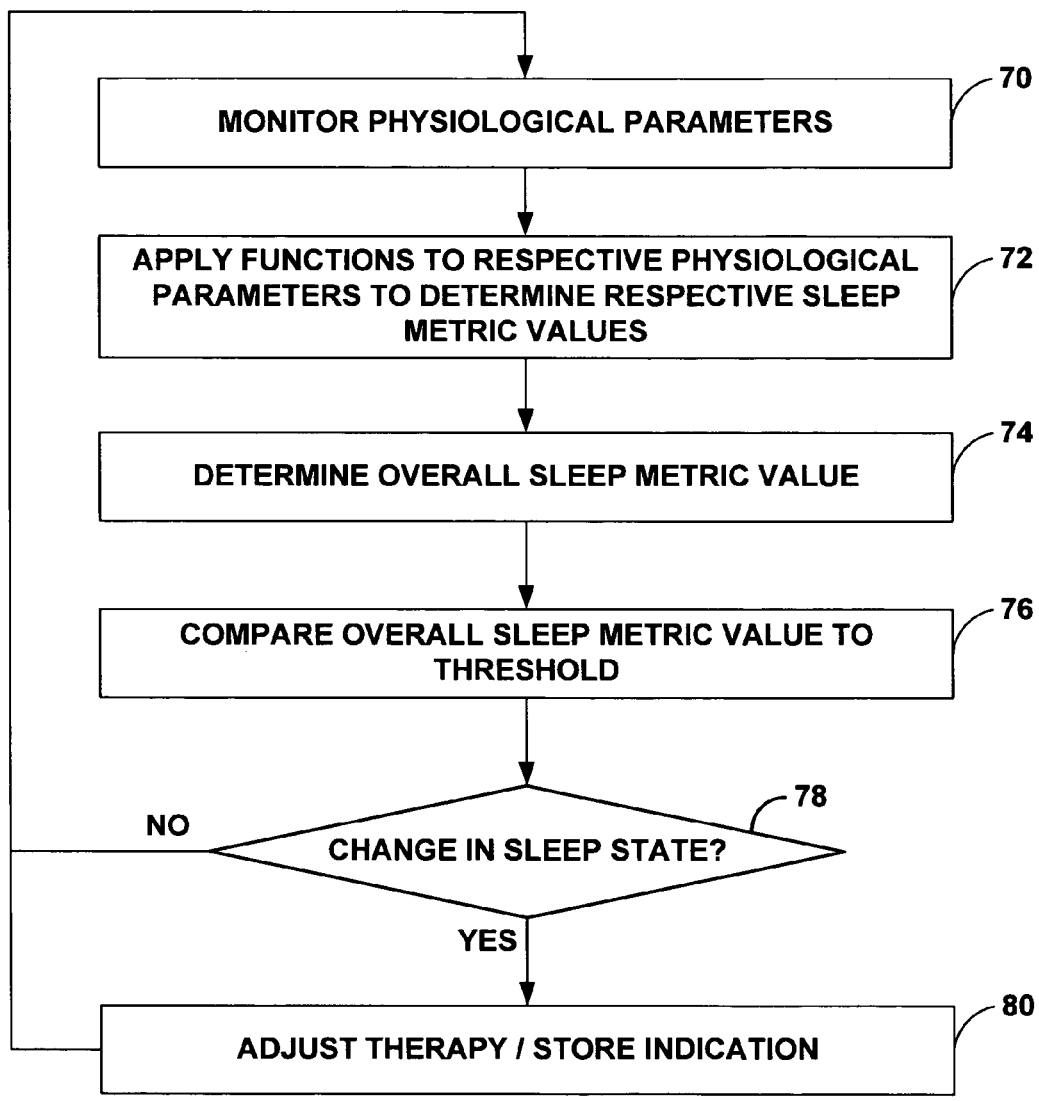
FIG. 4 is a flowchart illustrating an example technique for determining whether a patient is asleep.

FIG. 4 is a flowchart illustrating an example technique for determining whether a patient is asleep that may be employed by IMD 14. According to the example technique, IMD 14 monitors a plurality of physiological parameters of patient 12 (70). More particularly, processor 46 receives signals from one or more sensors 40, and monitors the physiological parameters based on the signals.

Processor 46 applies a respective function 62 to current values, mean or median values, and/or variability values for each of physiological parameters to determine a sleep metric value for each of the parameters (72). Processor 46 then combines the various sleep metric values to determine a current overall sleep metric value (74). For example processor 46 may apply weighting factors 66 to one or more of the parameter specific sleep metric values, and then average the parameter specific sleep metric values in light of the weighting factors 66.

Processor 46 compares the current overall sleep metric value to a threshold value 64 (76), and determines whether patient 12 is asleep or awake, e.g., whether the sleep state of patient 12 has changed, based on the comparison (78). For example, processor 46 may determine that patient 12 is asleep if the current overall sleep metric value exceeds the threshold value 64. If the sleep state of patient 12 has changed, processor 46 may initiate, suspend or adjust a therapy delivered to patient 12 by IMD 14, or processor 46 may store an indication of the time and the change within memory 48 (80).

Various embodiments of the invention have been described. However, one skilled in the art will appreciated that various modifications may be made to the described embodiments without departing from the scope of the invention. For example, although described herein in the context of an implantable neurostimulator, the invention may be embodied in any implantable or external device.

As another example, although described in the context of determining whether a patient is asleep, e.g., whether the patient's current sleep state is asleep or awake, the invention may, as described above, be used to determine what level of sleep a patient is currently experiencing, e.g., which of sleep states REM, S1, S2, S3, and S4 the patient is currently in. A medical device may record transitions between these states and between sleep and wakefulness, or may control therapy based on transitions between these states and between sleep and wakefulness. Further, in some embodiments, a medical device may, without making a sleep determination, simply record one or more determined sleep metric values for later analysis, or may control delivery of therapy based on the sleep metric values.

Further, the invention may be embodied in a programming device, such as programmers 20, 26 described above, or another type of computing device. In particular, in some embodiments, a computing device may determine when patient 12 is asleep according to the invention instead of, or in addition to an implantable or external medical device. For example, a medical device may record values for one or more of the physiological parameters discussed herein, and may provide the physiological parameter values to the computing device in real time or when interrogated by the computing device. The computing device may apply the techniques described herein with reference to IMD 14 to determine when patient 12 is asleep, and may control delivery of therapy based on the determination, or present information relating to the patient's sleep patterns to a user to enable diagnosis or therapy evaluation. The computing device may be a programming device, such as programmers 20, 26, or may be any handheld computer, desktop computer, workstation, or server. A computing device, such as a server, may receive information from the medical device and present information to a user via a network, such as a local area network (LAN), wide area network (WAN), or the Internet.

The invention may also be embodied as a computer-readable medium, such as memory 48, that includes instructions to cause a processor, such as processor 46, to perform any of the methods described herein. These and other embodiments are within the scope of the following claims.

The invention claimed is:

1. A medical system comprising:
   a plurality of sensors, each of the sensors generating a signal as a function of at least one physiological parameter of a patient; and
   an implantable medical device including a processor configured to:
      monitor a plurality of physiological parameters of the patient based on the signals output by the sensors,
      for each of the plurality of physiological parameters, determine a respective one of a plurality of sleep metric values, each of the sleep metric values indicating a probability of the patient being asleep based on the respective physiological parameter, and
      mathematically combine the plurality of sleep metric values that each indicates the probability of the patient being asleep based on the respective one of the plurality physiological parameters to determine an overall sleep metric value that indicates an overall probability of the patient being asleep,
   wherein the physiological parameters comprise at least one of electrocardiogram morphology, core temperature, subcutaneous temperature, muscular tone, brain electrical activity, or eye motion.

2. The system of claim 1, wherein the processor is configured to apply a weighting factor to at least one of values of the plurality of sleep metrics.

3. The system of claim 1, further comprising a memory to store a threshold value, wherein the memory is in operable communication with the processor, and wherein the processor is configured to compare the value of the overall sleep metric to the threshold value and determine whether the patient is asleep based on the comparison.

4. The system of claim 3, wherein the memory stores a plurality of threshold values, and the processor is configured to compare the value of the overall sleep metric to each of the threshold values and determine a sleep state of the patient based on the comparison.

5. The system of claim 4, wherein the processor is configured to determine whether the patient is in one of a rapid eye movement sleep state or a nonrapid eye movement sleep state.

6. The system of claim 1, wherein the implantable medical device comprises at least one of an implantable neurostimulator or an implantable pump.

7. A system comprising:
   means for monitoring a plurality of physiological parameters of a patient; and
   implantable means for determining a respective one of a plurality of sleep metric values for each of the plurality of physiological parameters, each of the sleep metric values indicating a probability of the patient being asleep based on the respective physiological parameter,
   further comprising means for mathematically combining the plurality of sleep metric values that each indicates the probability of the patient being asleep based on the respective one of the plurality physiological parameters to determine an overall sleep metric value that indicates an overall probability of the patient being asleep,
   wherein the physiological parameters comprise at least one of electrocardiogram morphology, core temperature, subcutaneous temperature, muscular tone, brain electrical activity, or eye motion.

* * * * *